United States Patent [19]

Ishikawa et al.

[11] Patent Number: 4,540,524

[45] Date of Patent: Sep. 10, 1985

[54] METHODS FOR PREPARING LOWER ALKYL α-FLUORO-α-CYANOACETATE AND ITS CARBANION

[75] Inventors: Nobuo Ishikawa, Yokohama; Akio Takaoka, Kawasaki, both of Japan

[73] Assignee: Daikin Kogyo Co., Ltd., Osaka, Japan

[21] Appl. No.: 669,178

[22] Filed: Nov. 7, 1984

Related U.S. Application Data

[63] Continuation-in-part of Ser. No. 528,060, Aug. 31, 1983, abandoned.

[30] Foreign Application Priority Data

Aug. 31, 1982 [JP] Japan .................................. 57-151003
Aug. 31, 1982 [JP] Japan .................................. 57-151004

[51] Int. Cl.$^3$ ............................................ C07C 121/00
[52] U.S. Cl. ................................................. 260/465.4
[58] Field of Search ................... 260/465.4, 465.0, 464

[56] References Cited

U.S. PATENT DOCUMENTS

| | | | |
|---|---|---|---|
| 2,965,670 | 12/1960 | McDonald et al. | 260/465.4 |
| 3,030,408 | 4/1962 | Inman et al. | 260/465.8 R |
| 3,094,551 | 6/1963 | Sauers et al. | 260/465.4 |
| 3,114,763 | 12/1963 | Josey | 260/465.6 |
| 3,141,040 | 7/1964 | Inman et al. | 260/455 R |
| 3,639,361 | 2/1972 | Robertson et al. | 260/465.4 |
| 3,654,340 | 4/1972 | Banitt | 260/465.4 |
| 3,658,878 | 4/1972 | Smith | 260/465.4 |
| 3,663,592 | 5/1972 | Banitt | 260/465.4 |
| 3,668,231 | 6/1972 | Rosin et al. | 260/465.4 |
| 3,722,599 | 3/1973 | Robertson et al. | 260/465.4 |
| 4,058,578 | 11/1977 | Kuhls et al. | 525/276 |
| 4,357,282 | 11/1982 | Anderson et al. | 260/465.4 |

OTHER PUBLICATIONS

Gershon, et al., Journal of Medicinal Chemistry, 10, (1967), pp. 536–541.
Gershon, et al., Journal of Medicinal Chemistry 13, (1970) pp. 1237–1239.
"Biochemistry Involving Carbon Fluorine Bond" by Ernest Kun, ACS Symp., Ser. 28, P1 (1976).

*Primary Examiner*—Joseph L. Schofer
*Assistant Examiner*—N. Sarofim
*Attorney, Agent, or Firm*—Armstrong, Nikaido, Marmelstein & Kubovcik

[57] ABSTRACT

A method for preparing lower alkyl α-fluoro-α-cyanoacetate and its carbanion by reacting hexafluoropropene with ammonia, and then reacting the obtained product with an alkali hydroxide in a lower alkyl alcohol. The carbanion is prepared by reacting the product α-fluoro-α-cyanoacetate with an alkali fluoride.

3 Claims, No Drawings

METHODS FOR PREPARING LOWER ALKYL α-FLUORO-α-CYANOACETATE AND ITS CARBANION

This application is a Continuation-In-Part of prior application Ser. No. 528,060, filed Aug. 31, 1983, now abandoned, claiming priority based upon Japanese patent applications Nos. 151003/1982 and 151004/1982, filed Aug. 31, 1982.

BACKGROUND OF THE INVENTION

This invention relates to α-fluoro-α-cyanoacetates and their carbanions, and more particularly lower alkyl α-fluoro-α-cyanoacetates and their carbanions.

There are known many monofluoro compounds that have physiological activities or are efficacious as agricultural chemicals or medicines. It is also known that α-fluoro-α-cyanoacetates and their carbanions are important intermediates serving as building blocks in the synthesis of such monofluoro compounds.

SUMMARY OF THE INVENTION

Accordingly, it is an object of the present invention to provide a new and useful method for preparing fluorine containing cyanoacetates and their carbanions. Specifically, the invention provides a method for preparing alkyl α-fluoro-α-cyanoacetates represented by the formula:

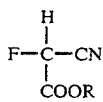

wherein R is an alkyl containing up to five carbon atoms and preferably 2 to 3 carbon atoms, by reacting hexafluoropropene (HFP) with ammonia, and then reacting the obtained product with an alkali hydroxide in an alkyl alcohol of the formula ROH.

Further, the carbanion corresponding to the product α-fluoro-α-cyanoacetate and represented by the following formula:

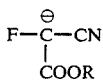

is prepared by reacting said product with an alkali fluoride.

DESCRIPTION OF THE PREFERRED EMBODIMENT

The method of this invention uses hexafluoropropene (HFP) as a starting material. The first step of this method consists of reacting HFP with ammonia by bubbling HFP into ammonia aqueous solution to form tetrafluoropropionitrile 1. In the second step, compound 1 is reacted with an alkali hydroxide solution in a lower alkyl alcohol. The reaction mixture is then acidified, resulting in a mixture of the desired product (α-fluoro-α-cyanoacetate) 2 and a by-product 3 which is a malonic ester. The α-fluoro-α-cyanoacetate can be isolated from the mixture and purified by redistillation. These reactions are illustrated below:

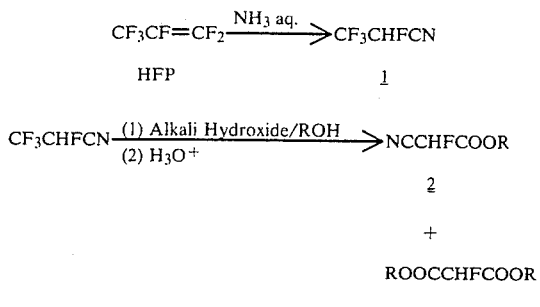

In the first step, tetrafluoropropionitrile can be obtained in greater yield and shorter reaction time if a dry ice-acetone condenser is used and the reaction is carried out in the presence of dioxane at a controlled reaction temperature. Thus, the HFP is bubbled into an ammonia-dioxane solution at a controlled temperature, preferably at $-5°$ to $10°$ C. Further, as disclosed by Knunyants and others, if ammonia is used in excess, particularly more than several times, for example, five to twenty times its stoichiometric quantity, the yield of tetrafluoropropionitrile is increased to about 75-80%.

In the second step of this method, the yield of the desired product, α-fluoro-α-cyanoacetate, is increased in relation to the yield of the by-product, malonic ester, by removing the alcohol following the alcoholysis reaction, and before adding acid to the reaction solution. Thus, in the instance where the alcohol used is ethyl alcohol, the product ethyl α-fluoro-α-cyanoacetate is produced in a yield of almost 70% as a result of this improvement in the method of the invention. Further, in this instance, the boiling point of the product ethyl α-fluoro-α-cyanoacetate and of the by-product ethyl monofluoromalonate differ by $35°$ C. After redistillation, the product ethyl α-fluoro-α-cyanoacetate is obtained in a yield of 60% (boiling point = $174°-175°$ C.)

To prepare the carbanion corresponding to product 2, said product is reacted with an alkali fluoride for ten minutes and under agitation at room temperature. One advantageous method for carrying out this reaction is by using a catalytic amount of spray dried potassium fluoride (KF) in sulfolane.

A possible reaction scheme for the mechanism by which compound 2 is formed from compound 1 is shown below, in which the reaction proceeds through formation of perfluoroacrylonitrile as an intermediate. It is assumed that ethyl fluorocyanoorthoacetate 4 is then formed. If compound 4 is hydrolyzed by an acid, such as HCl, $H_2SO_4$ or the like, compound 2 is produced. In addition, the hydrochloride of ethyl α-fluorocarboethoxyimidoacetate is also formed and, as its cyano group is decomposed, compound 3 is produced.

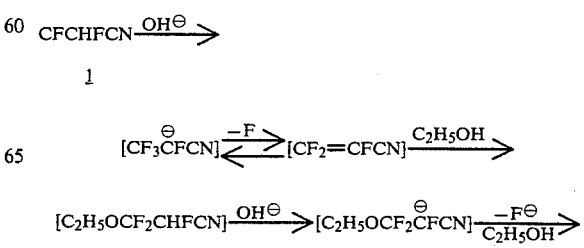

-continued $$[C_2H_5O)_3CCHFCN \xrightarrow{H_3O^+} C_2H_5O_2CCHFCN$$

$$\underline{4} \qquad \underline{2}$$

$$+$$

$$C_2H_5O_2CCHFCO_2C_2H_5$$

$$\underline{3}$$

The method of this invention for manufacturing a lower alkyl α-fluoro-α-cyanoacetate is advantageous because industrially produced and commercially available HFP is used as the starting material; the cost of producing the compound is low; and the conditions under which the reactions take place are mild.

The α-fluoro-α-cyanoacetates produced by the method of this invention are useful intermediates for the synthesis of fungicides and herbicides. In addition, the α-fluoro-α-cyanoacetates are useful as suicide inactivators for enzymes. Specifically, these alkyl α-fluoro-α-cyanoacetates serve as intermediates for the synthesis of longer-chain alkyl α-fluoro-α-cyanoacetates, which show antifungal activity against fungi such as Aspergilluniger, Trichoderma viride and Mycothecium verrucaria. The α-fluoro-α-cyanoacetates also serve as intermediates for preparing alkylated or alkenylated α-fluoro-α-cyanoacetates which are useful as herbicides and are represented by the following formula:

$$\begin{array}{c} R' \\ | \\ F-C-CN \\ | \\ COOR \end{array}$$

wherein R' is an aliphatic hydrocarbon group having up to 10 carbon atoms.

In addition, the α-fluoro-α-cyanoacetates prepared by the method of this invention can also function as a suicide inactivator in the manner shown below for an enzyme, for example, an enzyme which assists the increase of cancer cells:

$$\begin{array}{c} R' \\ \diagdown \\ C \\ \diagup \\ F \end{array} \begin{array}{c} CN \\ \diagup \\ CO_2R \end{array} \xrightarrow{EnZ-B^\ominus} \begin{array}{c} R' \\ \diagdown \\ C \\ \diagup \\ B \end{array} \begin{array}{c} CN \\ \diagup \\ CO_2R \end{array} + F^\ominus$$

$$EnZ$$

wherein EnZ—B$^\ominus$ is an enzyme assisting cancer cell growth and B$^\ominus$ is a base contained inside of the human body, for example, SH$^\ominus$, OH$^\ominus$ or NH$^\ominus$. Chemical bonding of EnZ—B$^\ominus$ with the α-fluoro-α-cyanoacetate, as shown above, results in the inactivation of EnZ—B$^\ominus$ and the prevention of cancer cell growth. A similar reaction is disclosed for fluoro carboxylic acid in "Biochemistry Involving Carbon Fluorine Bond" by E. Kun, ACS Symp., Ser. 28, P1 (1976):

$$FCH_2CO_2H + EnZ-B^\ominus \longrightarrow \begin{array}{c} FCHCO_2H \\ | \\ B-EnZ \end{array}$$

The carbanion prepared by the method of this invention is useful as an intermediate in the synthesis of Michael adducts which are useful as herbicides and insecticides. Said Michael adducts are prepared by adding to the above carbanion in an ice cooled condition various compounds which are known as Michael acceptors and are represented by the formula:

YCH=CHR'' wherein R'' is a hydrogen or an alkyl group, Y is selected from the group consisting of alkylcarbonyl, alkoxycarbonyl or cyano, and Y may form a ring by bonding to the carbon atom to which R' is bonded.

Another type of Michael acceptor is represented by the following formula:

YC≡CR'' wherein R'' is the same as described above.

The reactions by which the Michael adducts are produced proceed as follows:

$$N\overset{\ominus}{C}FCOOR + YCH=CHR'' \xrightarrow{H+} \begin{array}{c} R'' \ CN \\ | \ \ | \\ YCH_2CH-CF-COOR \end{array}$$

$$N\overset{\ominus}{C}CFCOOR + YC\equiv CR'' \xrightarrow{H+} \begin{array}{c} R'' \ CN \\ | \ \ | \\ YCH=C-CFCOOR \end{array}$$

The invention will be further clarified by a consideration of the following illustrative examples, which are not intended to limit the scope of the invention.

EXAMPLE 1

(a) Preparation of Tetrafluoropropionitrile

In a three-necked flask equipped with an efficient dry-ice condenser, 1000 g of concentrated ammonia water and 500 ml of 1,4 dioxane were placed. Into this mixture, 291 g of hexafluoropropene (HFP) gas were introduced at the rate of 0.9 g/min, keeping the temperature at 0±2° C. After the addition of HFP, the reaction mixture was stirred for 2 hrs at −5° to 0° C., then extracted with xylene, washed with water, dried over magnesium sulfate and subjected to distillation.

183 g of 2,3,3,3-tetrafluoropropio-nitrile, b.p. 39°–40° C., was obtained in a 74% yield.

Instead of 1,4-dioxane in the preceding procedure, the same amount of tetrahydrofuran was used. 295 g of hexafluoropropene was reacted in a similar manner, giving 206 g (82% yield) of 2,3,3,3-tetrafluoropropionitrile.

(b) Preparation of α-fluoro-α-Cyanoacetate

In a 2-liter flask a solution of 120 g of sodium hydroxide in 1 liter of ethanol was placed, and 127 g of 2,3,3,3-tetrafluoropropionitrile was added dropwise at room temperature and stirred for 1 hr. From the reaction mixture 500 ml of ethanol was distilled out and the residue was poured into 1 liter of water. Oily material was extracted from the residue with chloroform, washed with water 5 times, and dried over calcium chloride.

Into the extract thus obtained was added 80 ml of conc. hydrochloric acid and the mixture was stored at room temperature for 1 hour. After neutralization with a saturated aqueous solution of sodium bicarbonate, an oily layer was separated, washed with water and dried over magnesium sulfate. On removing chloroform, 79 g (60%) of ethyl α-fluoro-α-cyanoacetate and 46 g of (26%) of ethyl fluoro-malonate were distilled out at 174°–175° C. and 208°–210° C., respectively. The product, ethyl α-fluoro- α-cyanoacetate, showed the following properties.

IR(neat): 2260 (CN), 1780, 1760 cm$^{-1}$ (Ester)

$^{19}$F NMR(CHCl$_3$): δ114.0 (d) ($J_{HF}$=45.5 Hz)

$^{1}$H NMR(CDCl$_3$): δ5.47 (d) ($J_{HF}$—47.4 Hz), 4.30(q), 1.30 (t)

MS (m/e): 131 (M+)

What is claimed is:

1. A process for preparing an alkyl α-fluoro- α-cyanoacetate of the formula:

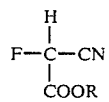

wherein R is an alkyl containing up to five carbon atoms, preferably 2 or 3 carbon atoms,
which comprises;
(a) reacting hexafluoropropene with ammonia to form 2,3,3,3-tetrafluoropropionitrile, and
(b) reacting the thus obtained 2,3,3,3-tetrafluoropropionitrile with an alkali hydroxide in an alkyl alcohol of the formula ROH.

2. A process as claimed in claim 1 wherein said alkyl alcohol has 2 or 3 carbon atoms.

3. A process as claimed in claim 1 wherein the reaction of said hexafluoropropene with said ammonia is carried out in dioxane or tetrahydrofuran at a temperature of −5° to 10° C.

* * * * *